US005795521A

United States Patent [19]
Mathieu

[11] Patent Number: 5,795,521
[45] Date of Patent: Aug. 18, 1998

[54] MOLDLESS BEVELING OF CATHETERS

[75] Inventor: Julien C. Mathieu, Avon, Conn.

[73] Assignee: Johnson & Johnson Medical, Inc., Arlington, Tex.

[21] Appl. No.: 709,172

[22] Filed: Sep. 6, 1996

[51] Int. Cl.$^6$ .................................................. B29C 57/00
[52] U.S. Cl. ........................ 264/163; 264/296; 264/310; 425/298
[58] Field of Search ................................. 264/163, 296, 264/310; 425/315, 316, 298; 83/162, 176

[56] References Cited

U.S. PATENT DOCUMENTS

| | | | |
|---|---|---|---|
| 3,595,116 | 7/1971 | Gilbert | 83/176 |
| 3,719,737 | 3/1973 | Vaillancourt et al. | 264/162 |
| 3,983,203 | 9/1976 | Corbett | 264/296 |
| 4,059,893 | 11/1977 | Solury | 30/90.1 |
| 4,551,292 | 11/1985 | Fletcher et al. | 264/162 |
| 4,661,300 | 4/1987 | Daugherty | 264/163 |
| 5,102,324 | 4/1992 | Bullard et al. | 264/40.6 |
| 5,151,231 | 9/1992 | Lambert et al. | 264/162 |
| 5,215,614 | 6/1993 | Wiljkamp et al. | 264/162 |
| 5,240,537 | 8/1993 | Bodicky | 264/162 |
| 5,397,512 | 3/1995 | Sloane, Jr. et al. | 264/161 |
| 5,456,875 | 10/1995 | Lambert | 264/328.1 |
| 5,589,120 | 12/1996 | Khan et al. | 264/130 |

Primary Examiner—Jan H. Silbaugh
Assistant Examiner—Mark Eashoo

[57] ABSTRACT

A moldless method for commercially producing intravenous catheters which are formed with geometrically identical catheter bevels. The method includes positioning an unbeveled catheter mounted on a central cylindrical support between first and second bevel profile blades. Each bevel profile blade has a blade surface in the shape of bevels to be imparted to the surface of the catheter, including a relatively steep bevel angle blade surface at the distal end of the catheter, which is the end to be inserted into a patient, and an adjacent relatively shallow bevel angle blade surface. The blade surfaces of the first and second bevel profile blades are positioned on opposite sides of the unbeveled catheter along a first axis. The first and second bevel profile blades are heated, and are translated in opposite directions towards the unbeveled catheter along a second axis which is substantially perpendicular to the first axis. During this operation, the translating blades squeeze and rotate the unbeveled catheter therebetween to pinch off and shape the catheter with the beveled surfaces defined by the bevel profile blades. The first and second bevel profile blades are then retracted from the beveled catheter, and the finished beveled catheter is removed from the beveling station.

15 Claims, 2 Drawing Sheets

MOLDLESS BEVELING OF CATHETERS

BACKGROUND OF THE INVENTION

1. Field of the Invention

The present invention relates generally to a method for moldless beveling of catheters, and more particularly pertains to a catheter beveling method for forming catheter bevels which are geometrically identical without the use of a catheter beveling mold. The subject invention provides a low cost, low waste, high efficiency approach for commercially producing beveled intravenous (IV) catheters, particularly thin walled catheters constructed of a plastic material such as polyurethane or Teflon®.

Intravenous catheters are particularly used in medical applications for introducing blood, plasma, or other fluids into the circulatory system of a patient. While IV catheters are available in several different types, one common type of catheter is constructed so as to be mounted upon a relatively long, hollow cannula (needle) with a slight frictional fit. A hub is attached to one end of the catheter and is designed so as to be connectable with and detachable from an IV fluid supply line. To insert the catheter into a patient, the cannula and catheter together are inserted through the patient's skin into a vein, and thereafter the cannula is withdrawn, leaving the catheter in place therein.

As manufactured, catheters have distal ends which are those ends to be inserted through the skin of a patient. The use of a catheter with a blunt distal or leading end is not desirable since the blunt tip tends to resist insertion into the skin, thereby increasing the difficulty and trauma of the insertion. Moreover, insertion of a blunt catheter tip increases the irritation to the surrounding tissue, and perhaps more importantly, adds significantly to the pain and discomfort of the patient during insertion.

Consequently, in the prior art the tips on IV catheters have been tapered or beveled to eliminate the aforementioned problems. The methods for providing such a beveled tip, however, are relatively few and often not publicly disclosed. Moreover, polyurethane catheters are particularly difficult to form, and thus there are relatively few known methods whereby a beveled tip can be formed on a polyurethane catheter.

Accordingly, a method for beveling an IV catheter is desirable which provides a uniform beveled tip, and is sufficiently fast and simple so as to permit commercial beveling of catheters in large quantities.

2. Discussion of the Prior Art

In the prior art, catheters with bevels have been produced by molding a catheter in a catheter beveling mold defining the beveled shape of the catheter and having a through pin projecting therethrough. The basic beveled shape of the catheter is molded in the catheter beveling mold by heating a polymeric tubing to allow it to deform and flow freely throughout the mold and define the basic bevel geometry of the catheter.

SUMMARY OF THE INVENTION

Accordingly, it is a primary object of the present invention to provide a method for moldless beveling of catheters.

A further object of the subject invention is the provision of a moldless method for commercially producing intravenous catheters which are formed with geometrically identical catheter bevels.

In accordance with the teachings herein, the present invention provides a method of beveling a catheter comprising positioning an unbeveled catheter mounted on a central cylindrical support between first and second bevel profile blades. Each bevel profile blade has a blade surface in the shape of bevels to be imparted to the surface of the catheter, including a relatively steep bevel angle blade surface at the distal end of the catheter, which is the end to be inserted into a patient, and an adjacent relatively shallow bevel angle blade surface. The blade surfaces of the first and second bevel profile blades are positioned on opposite sides of the unbeveled catheter along a first axis. The first and second heated bevel profile blades are heated, and are translated in opposite directions towards the unbeveled catheter along a second axis which is substantially perpendicular to the first axis. During this operation, the translating blades squeeze and rotate the unbeveled catheter therebetween to pinch off and shape the catheter with the beveled surfaces defined by the bevel profile blades. The first and second bevel profile blades are then retracted from the beveled catheter, and the finished beveled catheter is removed from the beveling station.

In greater detail, each bevel profile blade includes an end surface, with the relatively steep bevel angle blade surface extending to and forming a lateral blade edge with the end surface. The lateral blade edge extends along the direction of translation of the bevel profile blade, and projects to a position immediately adjacent to the central cylindrical support. Each bevel profile blade also includes an angled blade edge extending from the front of the blade, as defined by the direction of translation thereof, to the lateral blade edge. In a preferred embodiment the relatively steep bevel angle forms an angle of substantially 27° with respect to the longitudinal axis of the mounted catheter, and the relatively shallow bevel angle forms an angle of substantially 3° with respect to the longitudinal axis of the mounted catheter.

The central cylindrical support can comprise a plastic hub introducer needle (PHIN), which eliminates an extra handling step required by off cannula beveling, the step of inserting a cannula into the beveled catheter. Alternatively, the center cylindrical support can comprise a support pin.

In an automated beveling station, unbeveled catheters are introduced between the bevel profile blades, one at a time, by being indexed in a direction along the first axis, perpendicular to the direction of translation of the bevel profile blades. Each bevel profile blade is mounted for translation in a guide support which extends along the direction of translation of the bevel profile blades. Moreover, each guide support includes a heater element for heating the guide support and the bevel profile blade mounted therein.

Several advantages provided by the present invention include the ease of cleaning, inspection and maintenance of the bevel blades, the bevel blades are less expensive to produce than a catheter beveling mold, and the elimination of an extra handling step required by an off cannula beveling method.

BRIEF DESCRIPTION OF THE DRAWINGS

The foregoing objects and advantages of the present invention for moldless beveling of catheters may be more readily understood by one skilled in the art with reference being had to the following detailed description of several preferred embodiments thereof, taken in conjunction with the accompanying drawings wherein like elements are designated by identical reference numerals throughout the several views, and in which.

DETAILED DESCRIPTION OF THE DRAWINGS

Figure 2:
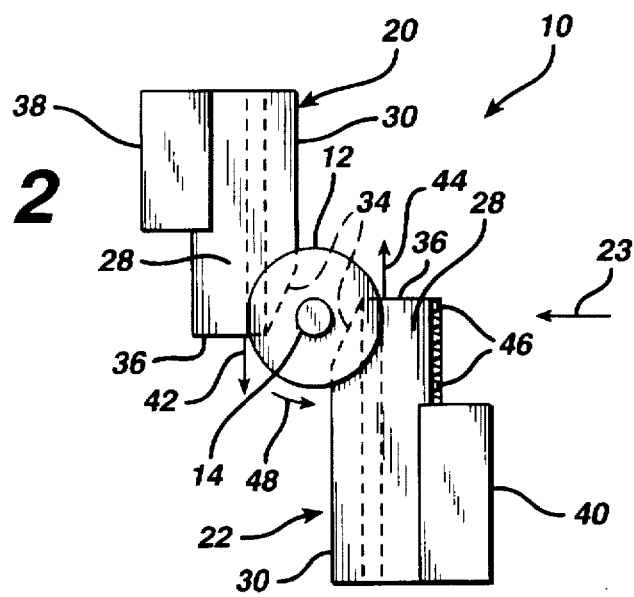
FIG. 2 is a top plan view of the catheter beveling station of FIG. 1.
Figure 1:
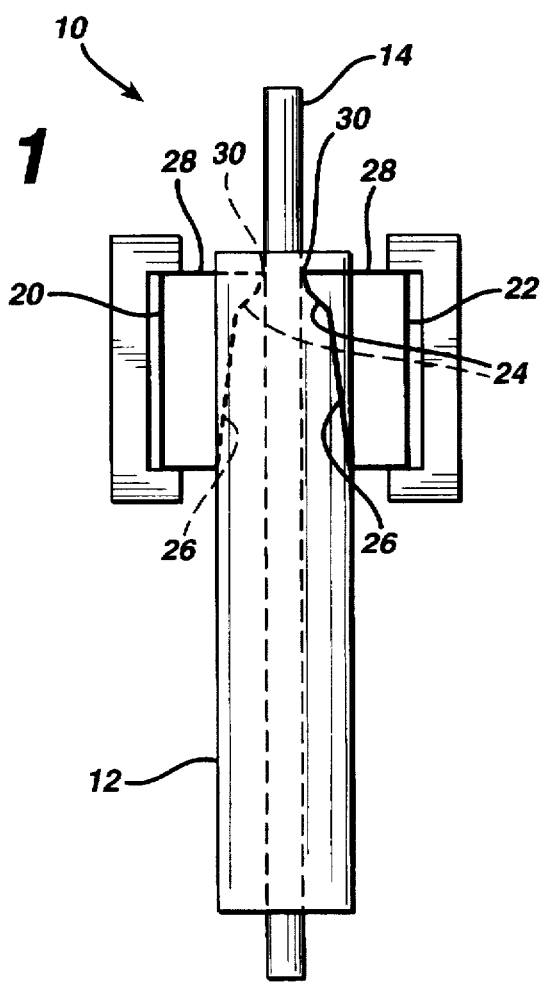
FIG. 1 is a front elevational view of a catheter beveling station wherein an unbeveled catheter enters the beveling station mounted on a support pin or plastic hub introducer needle (PHIN), and a pair of heated bevel blades, positioned on opposite sides of the unbeveled catheter, are indexed in opposite directions to roll, bevel and pinch off the catheter.
Figure 3:
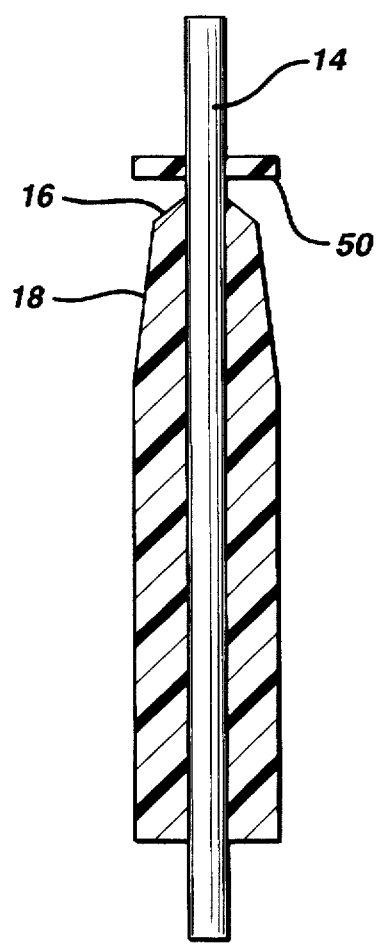
FIG. 3 is a front elevational view of the beveled catheter, supported on a pin or PHIN, after it has been beveled in the beveling station of FIGS. 1 and 2 and has been removed therefrom.
Figure 4:
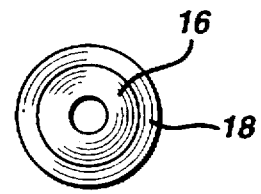
FIGS. 4 and 5 are respectively a front elevational view and a top plan view of a finished beveled catheter.
Figure 5:
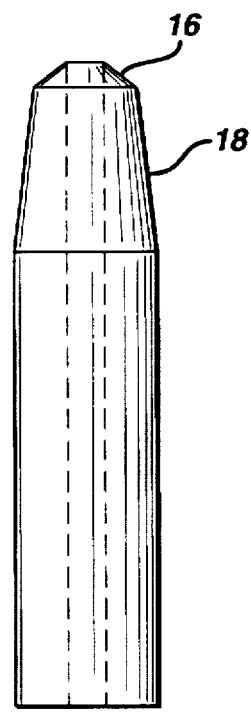

FIGS. 1 and 2 are respectively a front elevational view and a top plan view of a beveling station 10 for machining two beveled surfaces on an unbeveled catheter tube 12. Catheter tubes are frequently formed by extrusion of a suitable material such as polyurethane or Teflon®, after which the extruded tube is cut into suitable length catheter tubes. FIGS. 1 and 2 illustrate an unbeveled catheter tube 12 mounted on a central support 14, such as a support pin or plastic hub introducer needle (PHIN), and positioned in the beveling station 10, which is designed to form two beveled surfaces respectively 16 and 18 on the catheter tube. The distal end of a catheter, which is the end to be inserted through the skin of a patient, is typically formed with a first beveled surface 16 having a 27° bevel relative to the longitudinal axis of the catheter. The first beveled surface adjoins a second beveled surface 18, typically having a 3° bevel relative to the longitudinal axis of the catheter.

The beveling station 10 illustrated in FIGS. 1 and 2 includes first and second bevel profile blades 20, 22 which are mounted on first and second sides of the unbeveled catheter tube as it is mounted in the beveling station. In a commercial production facility, an unbeveled catheter tube 12 mounted on a central support 14 as shown, would be mechanically indexed, as by a suitable conveyer system, in the direction of arrow 23 into the position illustrated in FIGS. 1 and 2 where it is supported between the bevel profile blades 20, 22.

As illustrated in FIG. 1, each bevel profile blade 20, 22 defines a first blade surface 24 defining a relatively steep bevel angle with respect to the longitudinal axis of the catheter and a second blade surface 26 defining a relatively shallow bevel angle relative to the longitudinal axis of the catheter. Each bevel profile blade includes a top or end surface 28, with the relatively steep bevel angle blade surface 24 extending to and forming a lateral blade edge 30 with the end surface which extends along the direction of translation of the bevel profile blade, with the lateral blade edge 30 projecting to a position immediately adjacent to the central cylindrical support 14. Each bevel profile blade also includes an angled blade edge 34 extending from the front 36 of the blade, as defined by the direction of translation thereof, to the lateral blade edge 30. In a preferred embodiment, the relatively steep bevel angle forms an angle of substantially 27° with respect to the longitudinal axis of the mounted catheter, and the relatively shallow bevel angle forms an angle of substantially 3° with respect to the longitudinal axis of the mounted catheter.

Each of the first and second beveled profile blades 20, 22 is mounted in a heated guide support 38, 40. Each heated guide support 38, 40 includes a suitable heater, such as an electrical heating element, for heating the bevel profile blades to an appropriate temperature. Moreover, each heated guide support includes a suitable indexing mechanism for translating the bevel profile blade towards the unbeveled catheter as illustrated by the arrows 42, 44 in FIG. 2, and then retracting the blades after the beveling operation is completed. The indexing mechanism might be simply a linear track of gear teeth 46 positioned along the length of the bevel profile blade, such that a drive motor and gear controls translation of the blade. Prior to each beveling operation, the bevel profile blades 20, 22 are initially retracted within their respective heated guide supports 38, 40 in which they are heated to a suitable forming and machining temperature, such as a temperature equal to or greater than the melt temperature (TM) of the specific polymer.

The blade surfaces of the first and second bevel profile blades 20, 22 are positioned on opposite sides of the unbeveled catheter along a first axis extending in the direction of arrow 23. The first and second heated bevel profile blades 20, 22 are translated in opposite directions towards the unbeveled catheter along the direction of arrows 42, 44, along a second axis which is substantially perpendicular to the first axis. During this operation, the translating heated blades squeeze and rotate (as indicated by arrow 48) the unbeveled catheter therebetween around support 14 to pinch off and shape the catheter with the beveled surfaces 24 and 26 defined by the bevel profile blades. The first and second bevel profile blades are then retracted from the beveled catheter, and the finished beveled catheter is removed from the catheter beveling station.

The blades 20, 22 are advanced a sufficient distance to completely contact the entire circumferential girth of the catheter. Upon completion of the beveling operation, a small scrap piece 50 of the tubing remains mounted on the catheter support pin, and is later removed therefrom. The blades are then withdrawn back into the heated guide supports. The beveled catheter is indexed to the left, as illustrated in FIGS. 1 and 2, out of the beveling station, and another unbeveled catheter is indexed into the beveling station from the right side.

While several embodiments and variations of the present invention for moldless beveling of catheters are described in detail herein, it should be apparent that the disclosure and teachings of the present invention will suggest many alternative designs to those skilled in the art.

I claim:

1. A method of beveling a catheter having a distal end to be inserted into a patient comprising:

a. positioning an unbeveled catheter mounted on a central cylindrical support between first and second bevel profile blades, mounted for translation in opposite directions, wherein each bevel profile blade has a blade surface having a beveled shape which is to be imparted to a surface of the unbeveled catheter, including a relatively steep bevel angle blade surface at a distal end of the unbeveled catheter, and an adjacent relatively shallow bevel angle blade surface, wherein the blade surfaces of the first and second bevel profile blades are positioned on opposite sides of the unbeveled catheter in a first linear direction, and the first and second bevel blades are translated in opposite directions;

b. heating the first and second bevel profile blades; and c. then translating the first and second bevel profile blades in opposite directions parallel to an axis which is substantially perpendicular to the first linear direction towards the unbeveled catheter said translating causing the first and second bevel profile blades to pass tangentially along said catheter, wherein the first and second bevel profile blades squeeze and frictionally rotate the unbeveled catheter therebetween to pinch off and shape the beveled catheter with the beveled surfaces defined by the bevel profile blades, thereby forming a beveled catheter; and d. retracting the first and second bevel profile blades from the beveled catheter, and removing the beveled catheter from the central cylindrical support.

2. A method of beveling a catheter as claimed in claim 1, wherein each bevel profile blade includes an end surface, with the relatively steep bevel angle blade surface extending to and forming a lateral blade edge with the end surface which extends along the axis along the direction of translation of each bevel profile blade, with the lateral blade edge projecting to a position immediately adjacent to the central cylindrical support.

3. A method of beveling a catheter as claimed in claim 2, wherein each bevel profile blade includes an angled blade edge extending from a front, as defined by a direction of translation of the bevel profile blade, to the lateral blade edge.

4. A method of beveling a catheter as claimed in claim 3, wherein the relatively steep bevel angle is substantially 27° with respect to a longitudinal axis of the unbeveled catheter, and the relatively shallow bevel angle is substantially 3° with respect to the longitudinal axis of the unbeveled catheter.

5. A method of beveling a catheter as claimed in claim 4, wherein the central cylindrical support comprises a plastic hub introducer needle (PHIN).

6. A method of beveling a catheter as claimed in claim 4, wherein the central cylindrical support comprises a support pin.

7. A method of beveling a catheter as claimed in claim 4, wherein unbeveled catheters are introduced between the bevel profile blades, one at a time, by being indexed in a direction along the first linear direction perpendicular to the direction of translation of the bevel profile blades.

8. A method of beveling a catheter as claimed in claim 7, wherein each bevel profile blade is mounted for translation in a guide support which extends along the axis along the direction of translation of the bevel profile blades.

9. A method of beveling a catheter as claimed in claim 8, wherein each guide support includes a heater element for heating the guide support and the bevel profile blade mounted therein.

10. A method of beveling a catheter as claimed in claim 1, wherein the relatively steep bevel angle is substantially 27° with respect to a longitudinal axis of the unbeveled catheter, and the relatively shallow bevel angle is substantially 3° with respect to the longitudinal axis of the unbeveled catheter.

11. A method of beveling a catheter as claimed in claim 1, wherein the central cylindrical support comprises a plastic hub introducer needle (PHIN).

12. A method of beveling a catheter as claimed in claim 1, wherein the central cylindrical support comprises a support pin.

13. A method of beveling a catheter as claimed in claim 1, wherein unbeveled catheters are introduced between the bevel profile blades, one at a time, by being indexed in a direction along the first linear direction perpendicular to the direction of translation of the bevel profile blades.

14. A method of beveling a catheter as claimed in claim 1, wherein each bevel profile blade is mounted for translation in a guide support which extends along the axis along the direction of translation of the bevel profile blades.

15. A method of beveling a catheter as claimed in claim 14, wherein each guide support includes a heater element for heating the guide support and the bevel profile blade mounted therein.

* * * * *